United States Patent [19]

Heeres et al.

[11] Patent Number: 5,607,932
[45] Date of Patent: Mar. 4, 1997

[54] HETEROCYCLIC DERIVATIVES OF AZOLONES

[75] Inventors: Jan Heeres, Vosselaar; Raymond A. Stokbroekx, Beerse; Marc Willems, Vosselaar; Robert J. M. Hendrickx, Beerse, all of Belgium

[73] Assignee: Janssen Pharmaceutica N.V., Beerse, Belgium

[21] Appl. No.: 447,503

[22] Filed: May 23, 1995

[30] Foreign Application Priority Data

Jul. 12, 1994 [EP] European Pat. Off. .............. 94202018

[51] Int. Cl.$^6$ ...................... C07D 403/10; C07D 403/06; A61K 31/495; A61K 31/41
[52] U.S. Cl. ................ 514/252; 544/295; 544/296; 544/238; 544/357; 544/366; 544/364; 544/370
[58] Field of Search .................. 514/252; 544/366, 544/370, 364, 295, 296, 357, 238

[56] References Cited

U.S. PATENT DOCUMENTS

| | | | |
|---|---|---|---|
| 4,791,111 | 12/1988 | Heeres et al. | 514/252 |
| 4,931,444 | 6/1990 | Van Wauwe et al. | 514/252 |
| 5,254,553 | 10/1993 | Heeres et al. | 514/252 |

FOREIGN PATENT DOCUMENTS

WO94/18978  9/1994  WIPO ............ A61K 31/495

OTHER PUBLICATIONS

Chem. Abstracts, vol. 117, No. 7, 66400w, Rautelin et al. 1992.

*Primary Examiner*—Matthew V. Grumbling
*Attorney, Agent, or Firm*—Charles J. Metz

[57] ABSTRACT

The invention is concerned with the compounds having the formula the pharmaceutically acceptable addition salts and the stereochemically isomeric forms thereof, wherein Y is CH or N; $R_1$, $R^2$ and $R^3$ each independently are hydrogen or $C_{1-4}$alkyl; $R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy; $R^6$ is pyridinyl optionally substituted with up to two $C_{1-4}$alkyl groups; di($C_{1-4}$alkyl) hydroxypyridinyl; di($C_{1-4}$alkyl)$C_{1-4}$alkyloxypyridinyl; pyridazinyl optionally substituted with $C_{1-4}$alkyloxy; pyrimidinyl optionally substituted with hydroxy or $C_{1-4}$alkyloxy; thiazolyl optionally substituted with $C_{1-4}$alkyl; thiadiazolyl optionally substituted with $C_{1-4}$alkyl; benzoxazolyl or benzothiazolyl; or $R^6$ is pyrazinyl or pyridazinyl substituted with $C_{1-4}$alkyl; Z is C=O or CHOH; and is a radical of formula (a-1), (a-2), (a-3), (a-4), (a-5), (a-6), or (a-7).

Compositions comprising said compounds, processes for preparing the same and the use of these compounds as a medicine.

12 Claims, No Drawings

HETEROCYCLIC DERIVATIVES OF AZOLONES

CROSS-REFERENCE TO RELATED APPLICATION

This application claims priority from European Application No. 94.202.018.1, filed on Jul. 12, 1994.

The present invention is concerned with substituted azolone derivatives which are potent anti-Helicobacter agents.

U.S. Pat. No. 4,791,111 discloses azolones having a structure similar to that of the present compounds and which are intermediates in the preparation of [[4-[4-(4-phenyl-1-piperazinyl)phenoxymethyl]-1,3-dioxolan-2-yl]methyl]-1H-imidazoles and -1H-1,2,4-triazoles.

In U.S. Pat. No. 4,931,444 there are described substituted azolone derivatives having 5-lipoxy-genase inhibiting activity. The present compounds are distinguished therefrom by their useful anti-Helicobacter activity.

In the eradication of Helicobacter, dual therapies comprising the separate administration of two antibiotic drugs have not been satisfactory because of one or more of the following reasons: a low eradication rate, numerous side effects and development of resistance by Helicobacter. Triple therapies comprising the administration of two antibiotics and a bismuth compound have been shown to be effective, but are very demanding for the patients and are also compromised by side effects. The present compounds show the advantage that they may be used in a monotherapy in the eradication of *Helicobacter pylori* and related species.

The present invention is concerned with compounds having the formula

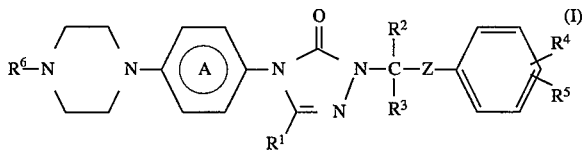

the pharmaceutically acceptable addition salts and the stereochemically isomeric forms thereof, wherein Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is pyridinyl optionally substituted with up to two $C_{1-4}$alkyl groups; di($C_{1-4}$alkyl) hydroxypyridinyl; di($C_{1-4}$alkyl)$C_{1-4}$alkyloxypyridinyl; pyridazinyl optionally substituted with $C_{1-4}$alkyloxy; pyrimidinyl optionally substituted with hydroxy or $C_{1-4}$alkyloxy;

thiazolyl optionally substituted with $C_{1-4}$alkyl; thiadiazolyl optionally substituted with $C_{1-4}$alkyl; benzoxazolyl or benzothiazolyl; or $R^6$ is pyrazinyl or pyridazinyl substituted with $C_{1-4}$alkyl;

Z is C=O or CHOH; and

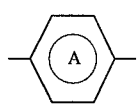

is a radical of formula

 (a-1)

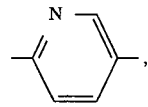 (a-2)

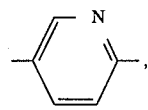 (a-3)

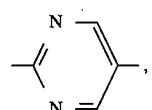 (a-4)

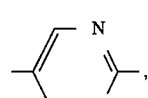 (a-5)

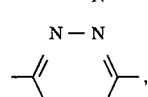 (a-6)

or

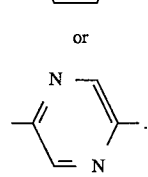 (a-7)

As used in the foregoing definitions halo defines fluoro, chloro, bromo and iodo;

$C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl. $C_{1-6}$alkyl defines $C_{1-4}$alkyl radicals as defined hereinbefore and the higher homologs thereof having from 5 to 6 carbon atoms such as, for example, pentyl and hexyl.

The term pharmaceutically acceptable addition salt as used hereinbefore defines the non-toxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

The absolute configuration of each chiral center may be indicated by the stereochemical descriptors R and S. For the compounds having two chiral centers, the relative stereodescriptors R* and S* are used in accordance with the Chemical Abstracts rules (Chemical Substance Name Selection Manual (CA), 1982 Edition, Vol. III, Chapter 20).

Some compounds of the present invention may exist in different tautomeric forms and all such tautomeric forms are intended to be included within the scope of the present invention.

A fast group of interesting compounds are those compounds of formula (I) wherein $R^4$ is halo and $R^5$ is hydrogen.

A second group of interesting compounds are those compounds of formula (I) wherein

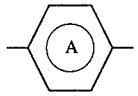

is a radical of formula (a-1) or (a-2).

A third group of interesting compounds are those compounds of formula (I) wherein Y is N and $R^1$ is hydrogen.

A fourth group of interesting compounds are those compounds of formula (I) wherein $R^2$ is $C_{1-4}$alkyl and $R^3$ is hydrogen.

A fifth group of interesting compounds are those compounds of formula (I) wherein $R^6$ is pyridinyl, thiazolyl or pyrimidinyl.

Also, a sixth group of interesting compounds are those compounds of formula (I) wherein $R^6$ is pyrazinyl.

Preferred compounds are those compounds of formula (I) wherein $R^1$, $R^3$ and $R^5$ are hydrogen; $R^2$ is $C_{1-4}$alkyl; $R^4$ is halo; and Y is N.

More preferred compounds are those compounds of formula (I) wherein $R^1$, $R^3$ and $R^5$ are hydrogen; $R^2$ is ethyl; $R^4$ is halo; Y is N; $R^6$ is pyridinyl, thiazolyl or pyrimidinyl; and

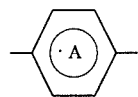

is a radical of formula (a-1) or (a-2).

The most preferred compounds are

2-[1-(4-chlorobenzoyl)propyl]-2,4-dihydro-4-[6-[4-(2-pyrimidinyl)-1piperazinyl]-3-pyridinyl]-3H-1,2,4-triazol-3-one;

2-[1-(4-chlorobenzoyl)propyl]-2,4-dihydro-4-[6-[4-(2-pyridinyl)-1-piperazinyl]-3-pyridinyl]-3H-1,2,4-triazol-3-one;

2-[1-[(4-chlorophenyl)hydroxymethyl]propyl]-2,4-dihydro-4-[6-[4-(2-pyridinyl)-1-piperazinyl]-3-pyridinyl]-3H-1,2,4-triazol-3-one; and 2-[1-[(4-chlorophenyl)hydroxymethyl]propyl]-2,4-dihydro-4-[6-[4-(2-thiazolyl)-1-piperazinyl]-3-pyridinyl]-3H-1,2,4-triazol-3-one;

the pharmaceutically acceptable addition salts and the stereochemically isomeric forms thereof.

Analogous procedures for the preparation of compounds such as the present compounds of formula (I) have been described in U.S. Pat. Nos. 4,791,111 and 4,931,444.

In particular, the compounds of formula (I) can be prepared by N-alkylating an intermediate of formula (II) with a reagent of formula (III).

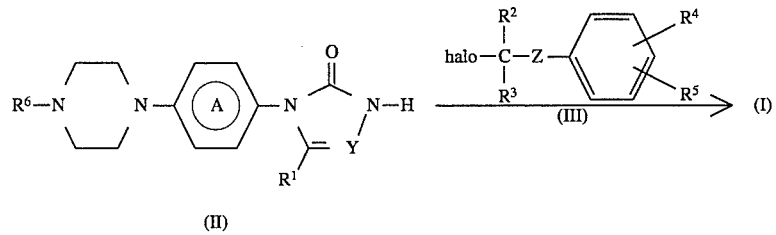

The N-alkylation reaction of (II) with (III) can conveniently be conducted by stirring and heating a mixture of the reagents in an appropriate solvent in the presence of a suitable base. Appropriate solvents are, for example dipolar aprotic solvents, e.g. N,N-dimethylformamide, N,N-dimethylacetamide, 1,3-dimethyl-2-imidazolidinone; aromatic solvents, e.g. benzene, methylbenzene; an ether, e.g 1,1'-oxybisethane, tetrahydrofuran, 1-methoxy-2-propanol; a halogenated hydrocarbon, e.g. dichloromethane, trichloromethane; or a mixture of such solvents.

Suitable bases are, for example, sodium bis(trimethylsilyl)amide, alkali metal and earth alkaline metal carbonates or hydrogen carbonates, e.g. sodium or potassium carbonate; or organic bases, e.g. triethylamine and the like bases.

The compounds of formula (I) may also be prepared by N-alkylating an intermediate of formula of formula (IV) with a reagent of formula (V).

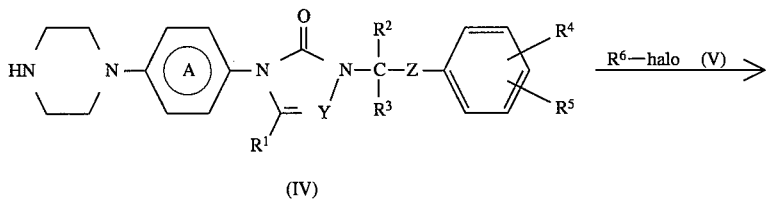

(IV)

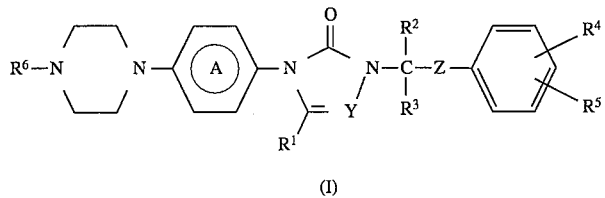

(I)

The above N-alkylation may conveniently be conducted using the solvents and bases described hereinabove for the N-alkylation of intermediate (II).

The compounds of formula (I) can also be convened into each other following art-known procedures of functional group transformation.

For example, the compounds of formula (I) wherein Z represents C=O can be converted into the compounds of formula (I) wherein Z represents CHOH following art-known reductions. For example, said reduction can conveniently be conducted by reaction with a metal hydride or complex metal hydride, e.g. sodium borohydride, sodium cyanoborohydride and the like in water, 1-methyl-pyrrolidinone, acetonitrile, an alcoholic medium, e.g. methanol, ethanol, or an ether, e.g. tetrahydrofuran, 1,4-dioxane; or in a mixture of such solvents.

Alternatively, said reduction can be conducted by reaction with tris(1-methylethoxy)potassium hydroborate, tris(1-methylpropyl)sodium hydroborate or tris(1-methylpropyl)potassium hydroborate in a reaction-inert solvent, e.g. tetrahydrofuran or N,N-dimethylformamide.

Further, the compounds of formula (I) wherein $R^6$ bears a hydroxy substituent can be prepared from the corresponding $C_{1-4}$alkyloxy derivatives by an appropriate dealkylation reaction, for example using trifluoroacetic acid, a mineral acid such as concentrated hydrohalic acid, e.g. hydrobromic acid, hydroiodic acid, optionally in admixture with a saturated solution of hydrobromic acid in glacial acetic acid; a Lewis acid, e.g. boron tribromide in a reaction-inert solvent, e.g. dichloromethane or N,N-dimethylacetamide. In the instance where hydrobromic acid is used it may be advantageous to conduct said dealkylation reaction in the presence of a bromine scavenger such as, for example sodium sulfite or hydrogen sulfite.

Finally, pure isomeric forms of the compounds of formula (I) can be separated from the mixture by conventional separation methods. In particular, the enantiomers may be separated by column chromatography using a chiral stationary phase such as a suitably derivatized cellulose, for example, tri(dimethylcarbamoyl)cellulose (Chiralcel OD®) and similar chiral stationary phases.

In all foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds. Other intermediates are novel, such as the intermediates of formula (II).

The intermediates of formula (II) can be prepared by cyclizing an intermediate of formula (VI) with a reagent of formula (VII) or a derivative thereof.

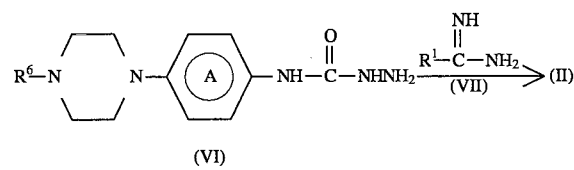

An appropriate reaction-inert solvent for the above cyclization reaction is, for example, a dipolar aprotic solvent, e.g. N,N-dimethylformamide, dimethyl sulfoxide and the like, or an alcohol, e.g. ethanol, 1-butanol and the like.

Alternatively, intermediates of formula (II) can be prepared by reacting an intermediate (IX) with a reagent of formula (V) following art-known procedures.

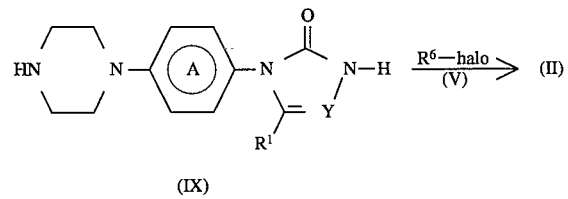

The intermediates of formula (II) can also be prepared by N-alkylating an intermediate of formula (X) with a reagent of formula (XI) following art-known N-alkylation procedures.

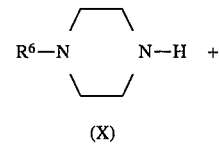

(X)

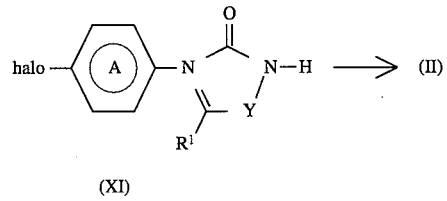

(XI)

The intermediates of formula (IV) may be prepared by the reaction of a compound of formula (VIII) with an acid, e.g. hydrobromic acid and the like.

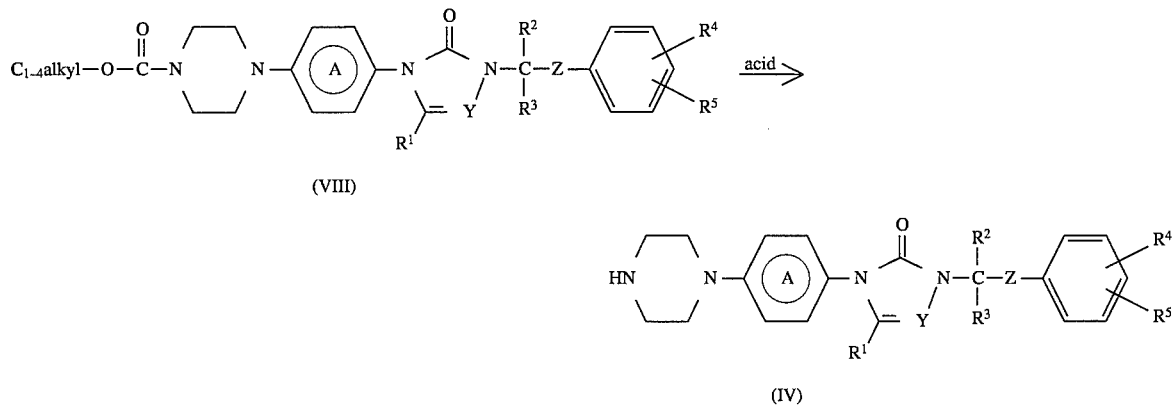

(VIII)

(IV)

The compounds of formula (I), the pharmaceutically acceptable addition salts and the stereochemically isomeric forms thereof display useful pharmacological activity against Helicobacter species; e.g. *Helicobacter pylori, Helicobacter mustelae, Helicobacter felis* and the like, in particular *Helicobacter pylori*.

Particularly important in this context is the finding that the subject compounds show inhibitory activity against the growth of Helicobacter as well as bactericidal activity against said bacteria. The bactericidal effect on Helicobacter was determined with suspension cultures by means of a procedure described in Antimicrob. Agents Chemother., 1991, vol. 35, pp. 869–872.

An interesting feature of the present compounds relates to their highly specific activity against Helicobacter. The compounds of formula (I) were found to show no inhibitory activity against any of the following species: *Campylobactor jejuni, Campylobacter coli, Campylobacter fetus, Campylobacter sputorum,* Vibrio spp., *Staphylococcus aureus* and *Escherichia coli*, tested at concentrations up to $10^{-5}$M.

An important asset of the present compounds is their sustained activity against *H. pylori* at pH below the neutral pH. Activity at a low pH in vitro may indicate that a compound is not adversely affected by the acidic environment of the stomach in vivo.

Consequently, the subject compounds are considered to be valuable therapeutical drugs for treating warm-blooded animals, particularly humans, suffering from Helicobacter related diseases or afflictions. Examples of said diseases or afflictions are gastritis, stomach ulcers, duodenal ulcers and gastric cancer.

In view of their useful anti-Helicobacter properties, the subject compounds may be formulated into various pharmaceutical forms for administration purposes. To prepare the pharmaceutical compositions of this invention, an effective amount of the particular compound, in base or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

When the pharmaceutical composition takes the form of an aqueous solution, those compounds of formula (I) which display low solubility may be formulated as a salt form, or a co-solvent may be added which is water-miscible and physiologically acceptable, e.g. dimethylsulfoxide and the like, or the compounds of formula (I) may be solubilized with a suitable carrier, e.g. a cyclodextrin (CD) or in particular a cyclodextrin derivative such as the cyclodextrin derivates described in U.S. Pat. No. 3,459,731, EP-A-149, 197 (Jul. 24, 1985), EP-A-197,571 (Oct. 15, 1986), U.S. Pat. No. 4,535,152 or WO 90/12035 (Oct. 18, 1990). Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyl-oxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin hydroxyalkyl derivatives for use in the compositions according to the present invention the M.S. as determined by mass spectrometry is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR or IR preferably range from 0.3 to 1, in particular from 0.55 to 0.75.

The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin derivatives for use in the compositions according to the present invention the D.S. as determined by MS is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR or IR preferably range from 0.3 to 1, in particular from 0.55 to 0.75. More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin is less than 5% of the total cyclodextrin content and in particular is less than 1.5%. Another particularly interesting cyclodextrin derivative is randomly methylated β-cyclodextrin.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Helicobacter related diseases it is evident that the present invention provides a method of treating warm-blooded animals, in particular humans, suffering from Helicobacter related diseases, said method comprising the systemic administration of a pharmaceutically effective amount of a compound of formula (I), a pharmaceutically acceptable addition salt thereof or a stereochemically isomeric form thereof, in admixture with a pharmaceutical carrier. In a further aspect of the invention, the subjects compounds are administered for use as a medicine.

In general it is contemplated that an effective daily amount would be from 0.05 mg/kg to 50 mg/kg body weight, preferably from 0.1 mg/kg to 30 mg/kg body weight and more preferably form 0.5 mg/kg to 10 mg/kg body weight.

It is evident that said effective daily amount may be lowered or increased depending on the response of the treated subject and/or depending on the evaluation of the physician prescribing the compounds of the instant invention. The effective ranges mentioned hereinabove are therefore guidelines only and are not intended to limit the scope or use of the invention to any extent.

Optionally, other active compounds used for the eradication of Helicobacter can be administered in combination with the compounds of the present invention. The administration may occur separately (i.e. simultaneously, concurrently or consecutively) or the different drugs may be combined in one dosage form. Suitable compounds for a combination therapy are bismuth compounds, e.g. bismuth subcitrate, bismuth subsalicylate, and the like, antibiotics, e.g. ampicillin, amoxicillin, clarithromycin and the like, $H_2$-receptor antagonists, e.g. cimetidine, ranitidine and the like, and in particular, proton pump inhibitors, e.g. omeprazole, lansoprazole, pantoprazole and the like. For the compounds cited to be useful for a combination therapy with the compounds of formula (I) an effective daily amount would be from 0.05 mg/kg to 50 mg/kg body weight.

Experimental part

Hereinafter, "DMF" means N,N-dimethylformamide, "DMSO" means dimethyl sulfoxide and "RT" means room temperature.

EXAMPLE 1 a) 2-(1-piperazinyl)pyrimidine (5.4 g), 4-(6-chloro-3-pyridinyl)-2,4-dihydro-3H-1,2,4-triazol-3-one (7 g) and sodium carbonate (4 g) were stirred at 190° C. for 1 hour.

The mixture was cooled and water was added. The precipitate was filtered off and recrystallized from 2-methoxyethanol. The precipitate was filtered off and dried, yielding 6.5 g (61%) of 2,4-dihydro-4-[6-[4-(2-pyrimidinyl)-1-piperazinyl-3-pyridinyl]-3,4-1,2,4-triazol-3-one (interm. 1).

b) A mixture of intermediate 1 (5.9 g), (±)-2-bromo-1-(4-chlorophenyl)-1-butanone (5.75 g) and sodium carbonate (4.3 g) in 1-methoxy-2-propanol (150 ml) was stirred and refluxed for 8 hours. The solvent was evaporated, water was added and the mixture was extracted with $CH_2Cl_2$. The organic layer was separated, dried, filtered and the solvent evaporated. The residue was crystallized from 2-propanol. The precipitate was filtered off and recrystallized from $C_2H_5OH$. The precipitate was filtered off and dried, yielding 7.6 g (84%) of (±)-2-[1-(4-chlorobenzoyl)propyl-2,4-dihydro-4-[6-[4(2-pyrimidinyl)-1-piperazinyl]-3-pyridinyl]-3H-1,2,4-triazol-3-one (comp. 1).

In a similar manner there were also prepared:

(±)-2-[1-(4-chlorobenzoyl)propyl]-2,4-dihydro-4-[6-[4-(5-methyl-1,3,4-thiadiazol-2-yl)-1-piperazinyl]-3-pyridinyl]-3H-1,2,4-triazol-3-one; mp. 200° C. (comp. 2);

(±)-2-[1-(4-chlorobenzoyl)propyl]-2,4-dihydro-4-[6-[4-(2-thiazolyl)-1-1-piperazinyl]-3-pyridinyl]-3H-1,2,4-triazol-3-one (comp. 3);

(±)-2-[1-(4-chlorobenzoyl)propyl]-2,4-dihydro-4-[6-[4-(6-methoxy-3-pyridazinyl)-1-piperazinyl]-3-pyridinyl]-3H-1,2,4-triazol-3-one; m.p. 133° C. (comp. 4);

(±)-2-[1-(4-chlorobenzoyl)propyl]-2,4-dihydro-4-[6-[4-(2-pyridinyl)-1-piperazinyl]-3H-pyridinyl]-3-1,2,4-triazol-3-one; mp. 134.1° C. (comp. 17);

2-[2-(4-chlorophenyl)-2-oxyethyl]-2,4-dihydro-4-[6-[4-(5-methoxy-4,6-dimethyl-2-pyridinyl)-1-piperazinyl]-

3-pyridinyl]-5-methyl-3H-1,2,4-triazol-3-one (comp. 18); and (±)-2-[1-(4-chlorobenzoyl)propyl]-2,4-dihydro-4-[6-[4-(3-pyridinyl)-1-piperazinyl]-3-pyridinyl]-3H-1,2,4-triazol-3-one (comp. 21).

EXAMPLE 2 a) A mixture of 5-methoxy-2-(1-piperazinyl)pyrimidine (8.8 g), 1-fluoro-4-nitrobenzene (7 g) and sodium carbonate (7.5 g) in DMSO (100 ml) was stirred at RT for 4 hours. The mixture was poured into water. The precipitate was filtered off and dissolved in $CH_2Cl_2$. $SiO_2$ (5 g) was added and the mixture was stirred, filtered and the solvent evaporated. The residue was boiled up in 1-propanol, filtered off and dried in vacuo at 75° C., yielding 8.5 g (60%) of 5-methoxy-2-[4-(4-nitrophenyl)-1-piperazinyl]pyrimidine; mp. 212.3° C. (interm. 2).

b) A mixture of intermediate 2 (68 g) in a 4% solution of thiophene (2 ml) and methanol (600 ml) was hydrogenated at 50° C. with palladium on activated carbon, palladium content 10% (4 g) as a catalyst. After uptake of hydrogen (3 eq.), the catalyst was filtered off and the filtrate was evaporated. The residue was stirred in $CH_3OH$, filtered off, dried in vacuo at 75° C. and crystallized from 1-propanol, treated with norit and filtered over decalite. The filtrate was crystallized. The precipitate was filtered off and dried in vacuo at 75° C., yielding 36.7 g (59%) of 4-[4-(5-methoxy-2-pyrimidinyl)-1-piperazinyl]benzenamine; mp. 125.2° C. (interm. 3).

c) Intermediate 3 (47.7 g) in N,N-dimethylacetamide (500 ml) was stirred on an ice/water bath. Phenyl chloroformate (23 ml) was added dropwise and the mixture was stirred for 3 hours. The mixture was poured into water and filtered off. The precipitate was dissolved in $CH_2Cl_2$. The aqueous layer was separated and evaporated. The residue was stirred up in diisopropyl ether, filtered off and dried, yielding 55.2 g (80%) of phenyl [4-[4-(5-methoxy-2-pyrimidinyl)-1-piperazinyl]phenyl]carbamate (interm. 4).

d) A mixture of intermediate 4 (55.2 g) in hydrazine monohydrate (60 ml) and 1,4-dioxane (1000 ml) was stirred at RT overnight. The mixture was poured into water and filtered off. The precipitate was dried in vacuo at 50° C., yielding 42 g (87%) of N-[4-[4-(5-methoxy-2-pyrimidinyl)-1-piperazinyl]phenyl]hydrazinecarboxamide (interm. 5).

e) A mixture of intermediate 5 (42 g), ethanimidate monohydrochloride (47 g) and sodium acetate (49.2 g) in 1-butanol (750 ml) was stirred and refluxed for 24 hours. The mixture was cooled, water was added and stirred. The precipitate was filtered off, dried in vacuo at 70° C., crystallized from DMF. The precipitate was filtered off and dried in vacuo at 75° C., yielding 19.6 g (45%) of 2,4-dihydro-4-[4-[4-(5-methoxy-2-pyrimidinyl)-1-piperazinyl]phenyl]-5-methyl-3H-1,2,4-triazol-3-one; mp.>300° C. (interm. 6).

f) Intermediate 6 (13 g) and DMF (400 ml) were stirred at RT. 1M of $NaN[Si(CH_3)_3]_2$ in tetrahydrofuran (38 ml) was added dropwise and the mixture was stirred for 1 hour at RT. 2-Bromo-1-(4-chorophenyl)ethanone (9.4 g) was added and the mixture was stirred for 5 hours at RT. The mixture was poured into water and filtered off. The precipitate was dissolved in $CH_2Cl_2$ and washed with water. The organic layer was dried, filtered and evaporated. The residue was purified by column chromatography over silica gel (eluent: $CH_2Cl_2$/ $CH_3OH$ 99/1). The suitable fractions were collected and evaporated. The residue was crystallized from 1-propanol, filtered off and dried in vacuo at 70° C., yielding 8.4 g (46%) of 2-[2-(4-chlorophenyl)-2-oxoethyl]-2,4-dihydro-4-[4-[4(5-methoxy-2-pyrimidinyl)-1-piperazinyl]phenyl]-5-methyl-3H-1,2,4-triazol-3-one; mp. 220° C. (comp. 5).

In a similar manner there was prepared:

(±)-2-[1-(4-chlorobenzoyl)propyl]-2,4-dihydro-4-[6-[4-(5-methoxy-2-pyrimidinyl)-1- piperazinyl]-3-pyridinyl]-3H-1,2,4-triazol-3-one; mp. 152° C. (comp. 6);

(±)-2-[1-(4-chlorobenzoyl)propyl]-2,4-dihydro-4-[6-[4-(4-methoxy-2-pyrimidinyl)-1-piperazinyl]-3-pyridinyl]-3H-1,2,4-triazol-3-one; mp. 162.5° C. (comp. 22); and (±)-2-[1-(4-chlorobenzoyl)propyl]-2,4-dihydro-4-[4-[4-(4-methoxy-2-pyrimidinyl)-1-piperazinyl]-phenyl]-3H-1,2,4-triazol-3-one; mp. 149.6° C. (comp. 23).

EXAMPLE 3 a) A mixture of (±)-ethyl 4-[4-[2-[1-(4-chlorobenzoyl)propyl]-2,3-dihydro-3-oxo-4H-1,2,4-triazol-4-yl]phenyl]-1-piperazinecarboxylate (15 g) in a hydrobromic acid solution 48% in water (150 ml) was stirred and refluxed overnight. The solvent was evaporated, the residue was dissolved in $CH_2Cl_2$ and washed with $NaHCO_3/H_2O$. The organic layer was dried, filtered and evaporated. The residue was dissolved in 2-propanol and crystallized into the hydrochloric acid salt (1:2) in 2-propanol. The precipitate was faltered off and recrystallized from $CH_3CN$, yielding 7.9 g (2.2%) of (±)-2-[1-(4-chlorobenzoyl)propyl]-2,4-dihydro-4-[4-(1-piperazinyl)phenyl]-3H-1,2,4-triazol-3-one dihydrochloride.monohydrate; mp. 175.9° C. (interm. 7).

b) A mixture of 2-chlorobenzothiazole (3.7 g), the free base of intermediate 7 (7.5 g) and sodium carbonate (5 g) in DMF (100 ml) was stirred at 70° C. overnight. The mixture was cooled, poured into ice/water and stirred for 1 hour. The mixture was filtered off and dissolved in $CH_2Cl_2$. The organic layer was dried, filtered and evaporated. The residue was crystallized from $C_2H_5OH$. The precipitate was filtered off and dried, yielding 6.5 g (78%) of (±)-4-[4-[4-(2-benzothiazolyl)-1-piperazinyl]phenyl]-2-[1-(4-chlorobenzoyl)-propyl]-2,4-dihydro-3H-1,2,4-triazol-3-one; mp. 162° C. (comp. 7).

In a similar manner there was also prepared:

(±)-4-[4-[4-(2-benzoxazolyl)-1-piperazinyl]phenyl]-2-[1-(4-chlorobenzoyl)propyl]-2,4-dihydro-3H-1,2,4-triazol-3-one; mp. 150° C. (comp. 8);

(±)-2-[1-(4-chlorobenzoyl)propyl]-2,4-dihydro-4-[6-[4-(4-pyridinyl)-1-1-piperazinyl]-3- pyridinyl]-3H-1,2,4-triazol-3-one; mp. 173.8° C. (comp. 23); and (±)-2-[1-(4-chlorobenzoyl)propyl]-2,4-dihydro-4-[6-[4-(6-methyl-3-pyridazinyl)-1-piperazinyl]-3-pyridinyl]-3H-1,2,4-triazol-3-one; mp. 212.1° C. (comp. 24).

EXAMPLE 4

A solution of tribromoborane (150 ml) in $CH_2Cl_2$ (100 ml) was stirred at RT. A solution of compound 5 (7.1 g) in $CH_2Cl_2$ (300 ml) was added and the resulting reaction mixture was stirred for 3 hours at RT. The mixture was added dropwise to a mixture of ice and ammonia (200 ml). The separated organic layer was dried over $MgSO_4$, filtered and the solvent was evaporated. The residue was purified by column chromatography over silica gel (eluent: $CH_2Cl_2$/ $CH_3OH$ 98/2). The pure fractions were collected and the solvent was evaporated. The residue was crystallized from 1-propanol. The crystals were filtered off and dried (vacuum; 70° C.), yielding 4.3 g (65%) of 2-[2-(4-chlorophenyl)-2-oxoethyl]-2,4-dihydro-4-[4-[4-(5-hydroxy-2-pyrimidinyl)-1-piperazinyl]phenyl]-5-methyl-3H-1,2,4-triazol-3-one; mp. 225° C. (comp. 9).

In a similar manner there were prepared:

(±)-2-[1-(4-chlorobenzoyl)propyl]-2,4-dihydro-4-[6-[4-(5-hydroxy-2-pyrimidinyl)-1-piperazinyl]-3-pyridinyl]-3H-1,2,4-triazol-3-one 1-propanolate(2:1); mp. 109° C. (comp. 10); and 2-[2-(4-chlorophenyl)-2-oxoethyl]-2,4-dihydro-4-[6-[4-(5-hydroxy-4,6-dimethyl-2-pyridinyl)-1-piperazinyl]-3-pyridinyl]-5-methyl-3H-1,2,4-triazol-3-one; mp. 212.1° C. (comp. 19).

EXAMPLE 5

A mixture of compound 9 (4.3 g) in $CH_3CN$ (150 ml) and $CH_3OH$ (36 ml) was stirred on an ice bath at 0° C. Sodium borohydride (1.6 g) in water (12 ml) was added dropwise at 0–10° C. and the mixture was stirred for 3 hours at RT. The mixture was poured into water and neutralized with $CH_3COOH$. The precipitate was filtered off and crystallized from 1-propanol. The mixture was cooled, filtered and dried in vacuo at 75° C., yielding 1.7 g (40%) of (±)-2-[2-(4-chlorophenyl)-2-hydroxyethyl]-2,4-dihydro-4-[4-[4-(5-hydroxy-2-pyrimidinyl)-1-piperazinyl]phenyl]-5-methyl-3H-1,2,4-triazol-3-one; mp. 249° C. (comp. 11).

In a similar manner them was prepared:

(±)-(R*,R*)-2-[1-[(4-chlorophenyl)hydroxymethyl]propyl]-2,4-dihydro-4-[6-[4-methoxy-3-pyridazinyl)-1-piperazinyl]-3-pyridinyl]-3H-1,2,4-triazol-3-one; mp. 244° C. (comp. 12); and (±)-(R *,R*)-2-[1-[(4-chlorophenyl)hydroxymethyl]propyl]-2,4-dihydro-4-[6-[4-(5-methyl-1,3,4-thiadiazol-2-yl)-1-piperazinyl]-3-pyridinyl]-3H-1,2,4-triazol-3-one; mp. 237.4° C. (comp. 25).

EXAMPLE 6

A mixture of compound 8 (3.2 g) in DMF (80 ml) was stirred at −20° C. Potassium tri(isobutyl)borohydride (20 ml) was added dropwise and the mixture was stirred at RT overnight. The mixture was poured into ice/water with HCl and stirred at RT for 1 hour. The precipitate was filtered off and crystallized from 2-methoxyethanol. The precipitate was filtered off and dried. The residue was purified by HPLC. The pure fractions were collected and evaporated. The residue was crystallized from 2-methoxyethanol. The precipitate was filtered off and dried, yielding 0.79 g (26%) of (±)-(R*,R*)-4-[4-[4-(2-benzoxazolyl)-1-piperazinyl]phenyl]-2-[1-[(4-chlorophenyl)-hydroxymethyl]propyl]-2,4-dihydro-3H-1,2,4-triazol-3-one; mp. 221° C. (comp. 13).

In a similar manner there were prepared:

(±)-(R*,R*)-2-[1-[(4-chlorophenyl)hydroxymethyl]propyl]-2,4-dihydro-4-[6-[4-(2-thiazolyl)-1-piperazinyl]-3-pyridinyl]-3H-1,2,4-triazol-3-one; mp. 215° C. (comp. 14);

(±)-(R*,R*)-2-[1-[(4-chlorophenyl)hydroxymethyl]propyl]-2,4-dihydro-4-[6-[4-(2-methoxy-2-pyrimidinyl)-1-piperazinyl]-3-pyridinyl]-3H-1,2,4-triazol-3-one; mp. 220° C. (comp. 15);

(±)-(R*,R*)-2-[1-[(4-chlorophenyl)hydroxymethyl]propyl]-2,4-dihydro-4-[6-[4-(2-pyrimidinyl)-1-piperazinyl]-3-pyridinyl]-3H-1,2,4-triazol-3-one; mp. 231° C. (comp. 16);

(±)-(R*,R*)-2-[1-[(4-chlorophenyl)hydroxymethyl]propyl]-2,4-dihydro-4-[6-[4-(2-pyridinyl)-1-piperazinyl]-3-pyridinyl]-3H-1,2,4-triazol-3-one; mp. 219.7° C. (comp. 20).

(±)-(R*R*)-2-[1-[(4-chlorophenyl)hydroxymethyl]propyl-4-[6-[4,6-dimethyl-2-pyridinyl)-1-piperazinyl]-3-pyridinyl]-2,4-dihydro-3H-1,2,4-triazol-3-one; mp. 171.4° C. (comp. 26);

(±)-(R*,R*)-2-[1-[(4-chlorophenyl)hydroxymethyl]propyl]-2,4-dihydro-4-[6-[6-(4-methoxy-2-pyrimidinyl)-1-piperazinyl]-3-pyridinyl]-3H-1,2,4-triazol-3-one; mp. 215.3° C. (comp. 27);

(±)-(R*,R*)-2-[1-[(4-chlorophenyl)hydroxymethyl]propyl]-2,4-dihydro-4-[4-[4-methoxy-2-pyrimidinyl)-1-piperazinyl]phenyl]-3H-1,2,4-triazol-3-one; mp. 161.2° C. (comp. 28);

(±)-(R*,R*)-2-[1-[(4-chlorophenyl)hydroxymethyl]propyl]-2,4-dihydro-4-[6-[4-(3-pyridinyl)-1-piperazinyl]-3-pyridinyl]*-1,2,4-triazol-3-one (comp. 29); and (±)-(R*,R*)-2-[1-[(4-chlorophenyl)hydroxymethyl]propyl]-2,4-dihydro-4-[6-[4-(2-pyrazinyl)-1-piperazinyl]-3-pyridinyl]-3H-1,2,4-triazol-3-one (comp. 30).

EXAMPLE 7 a) A mixture of ethyl 4-[5-(2,3-dihydro-3-oxo-4H-1,2,4-triazol-4-yl)-2-pyridinyl]-1-(15.7 g), prepared following a similar procedure as described in examples 2b) to 2e), in hydrobromic acid (48% solution in water) (100 ml) was stirred and refluxed for 2 hours. The mixture was cooled to RT and the solvent was evaporated, yielding 17.2 g (85.3%) of 2,4-dihydro-4-[6-(1-piperazinyl)-3-pyridinyl]-3H-1,2,4-triazol-3-one dihydrobromide; mp. >300° C. (interm. 8).

b) A mixture of intermediate 8 (9.81 g) and 2-chloropyrazine (10.31 g) in 1-methyl-2-pyrrolidinone (100 ml) and triethylamine (20 ml) was stirred and refluxed for 15 hours. The mixture was treated with water (200 ml) and filtered off. The precipitate was dissolved in $CH_2Cl_2$ and the layers were separated. The organic layer was dried over $MgSO_4$, filtered off and evaporated. The residue was purified by column chromatography over silica gel (eluent: $CH_2Cl_2/CH_3OH$ 100/0 to 93/7). The pure fractions were collected and evaporated, yielding 7.4 g (95.1%) of 2,4-dihydro-4-[6-[4-(2-pyrazinyl)-1-piperazinyl]-3-pyridinyl]-3H-1,2,4-triazol-3-one (interm. 9).

c) A mixture of intermediate 9 (7.1 g) and (±)-2-bromo-1-(4-chlorophenyl)-1-butanone (6.3 g) in DMF (200 ml) was stirred under $N_2$ for 5 minutes. Sodium carbonate (2.76 g) was added and the mixture was stirred and heated at 60° C. for 15 hours. The mixture was cooled on an ice bath, water (350 ml) was added slowly and filtered off. The residue was recrystallized from $CH_3OH$, yielding 7.9 g (71.4%) of (+)-2-[1-(4-chlorobenzoyl)propyl]-2,4-dihydro-4-[6-[4-(2-pyrazinyl)-1-piperazinyl]-3-pyridinyl]-3H-1,2,4-triazol-3-one; mp. 190.0° C. (comp. 31).

EXAMPLE 8

(±)-2-[1-(4-chlorobenzoyl)propyl]-2,4-dihydro-4-[6-(1-piperazinyl)-3-pyridinyl]-3H-1,2,4-triazol-3-one (6.02 g) and 2-bromo-4,6-dimethylpyridine (5.25 g) were stirred and heated under $N_2$ at 140° C. for 2 days. The mixture was dissolved in $CH_2Cl_2$ and purified on a glass filter over silica gel (eluent: $CH_2Cl_2/CH_3OH$ 100/0 to 97/3). The pure fractions were collected and evaporated, yielding 3.6 g (48%) of (±)-2-[1-(4-chlorobenzoyl)propyl]-4-[6-[4-(4,6-dimethyl-2- pyridinyl)-1-piperazinyl]-3-pyridinyl]-2,4-dihydro-3H-1,2,4-triazol-3-one; mp. 113.2° C. (comp. 32).

EXAMPLE 9 a) A mixture of 2-chloro-4-methoxypyrimidine (29 g) and 1-(5-nitro-2-pyridinyl)piperazine (35 g) in tetrahydrothiophene 1,1-dioxide (50 ml) was stirred at 130° C. for 1 hour. The mixture was poured into sodium carbonate and water, stirred for 30 minutes and extracted with $CH_2Cl_2$. The organic layer was dried over $MgSO_4$, filtered and evaporated. The residue was triturated in diisopropyl ether, yielding 23 g (43%) of 4-methoxy-2-[4-(5-nitro-2-pyridinyl)-1-piperazinyl]pyrimidine (interm. 10).

b) Starting from intermediate 10, (±)-2-[1-(4-chlorobenzoyl)propyl]-2,4-dihydro-4-[6-[4-(4-methoxy-2-pyrimidinyl)-1-piperazinyl]-3-pyridinyl]-3H-1,2,4-triazol-3-one was prepared following a procedure analogous to the one described in examples 2b) to 2f); mp. 162.5° C. (comp. 33).
Pharmacological example The anti-Helicobacter activity of the subject compounds was assessed by the following in vitro test procedure.

EXAMPLE 10

Activity of test compounds versus Helicobacter

The activity of test compounds against *Helicobacter pylori* was determined against a standard set of 5 *H. pylori* strains obtained from clinical material. Minimal inhibitory concentrations (MICs) were determined by measuring the activity of *H. pylori* urease after treatment of growing cultures of the bacteria with the antimicrobial agents.

The test compounds were dissolved in DMSO at a concentration of $10^{-3}$M. A dilution to $10^{-4}$M in DMSO was also prepared. 10 µl volumes of these solutions were pipetted in the wells of Repli-Dishes (®Sterilin). Wells containing DMSO alone were included as controls in each Repli-Dish. Ampicillin ((±)-6-[(2-amino-2-phenylacetyl)amino]-3,3-dimethyl-7-oxo-4-thia-1-azabicyclo[3.2.0]heptane-2-carboxylic acid trihydrate) and metronidazole (2-methyl-5-nitro-1H-imidazol-1-ethanol) were included as reference compounds in each batch of tests. (These compounds were tested at final concentrations of $10^{-5}$, $10^{-6}$, $10^{-7}$ and $10^{-8}$M). Test plates were stored at 4° C.

The five isolates of *H. pylori* were maintained by subculture on 10% blood agar every 2 or 3 days. The bacteria were grown at 37° C. under an atmosphere containing 5% oxygen, 10% $CO_2$ and 85% nitrogen. Suspensions of *Helicobacter pylori* for inoculum were prepared in Brain-heart infusion broth and adjusted to an absorbance of 1.5±0.3 at 530 nM.

Freshly prepared 10% blood agar held at 45° C. was added in 1 ml volumes to the wells of the test plates, thus diluting the test compounds to $10^{-5}$ and $10^{-6}$M. The medium was allowed to cool, then 10 µl volumes of bacterial suspension were pipetted on the agar surface. The plates were incubated for 48 hours at 37° C. under the microaerophilic atmosphere described above. To facilitate reading of the plates and to ensure that any growth on the media was truly *H. pylori*, advantage was taken of the highly potent urea activity unique to this species. After the 48 hours of incubation, 1 ml volumes of urease broth were gently added to each Repli-Dish well and the plates were incubated at 37° C. for 2 hours. 100 µl samples of fluid from each well were then pipetted into the wells of 96-place microdilution plates. A purple colour was interpreted as growth, yellow-orange as no growth of *H. pylori*. By this means a clear end-point was obtained, from which the inhibitory effects could be determined. All compounds that showed activity at either of the two concentrations tested were retested with further dilutions included to establish the MIC and with a broader spectrum of bacterial species as target organisms. Thus far, the MIC values for compounds 1–4, 8, 10, 12, 14–16, 20, 23 and 26–29 were found to be equal or below 1 µM.
Composition examples "Active ingredient" (A.I.) as used throughout these examples relates to a compound of formula (I), a pharmaceutically acceptable acid addition salt or a stereochemically isomeric form thereof.

EXAMPLE 11

ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then a solution of 1750 grams of sodium saccharin in 2.5 l of purified water was added. Upon stirring were added 2.5 l of cocoa flavor and polyethylene glycol q.s. to a volume of 50 l, providing an oral drop solution comprising 10 mg/ml of A.I. The resulting solution was filled into suitable containers.

EXAMPLE 12

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 13

FILM-COATED TABLETS
Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in 200 ml of water. The wet powder mixture was sieved, dried and sieved again. 100 Grams microcrystalline cellulose and 15 grams hydrogenated vegetable oil were added. The whole was mixed well and compressed into tablets, giving 10.000 tablets, each containing 10 mg of the active ingredient.
Coating To a solution of 10 grams methyl cellulose in 75 ml of denaturated ethanol was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 14

SUPPOSITORIES 3 Grams A.I. was dissolved in a solution of 3 grams 2,3-dihydroxybutanedioic acid in 25 ml polyethylene glycol 400. 12 Grams surfactant and triglycerides q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

We claim:

1. A compound having the formula

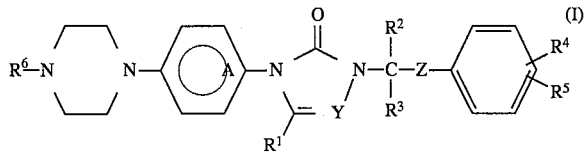

pharmaceutically acceptable addition salt or a stereochemically isomeric form thereof,
wherein Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is pyridinyl optionally substituted with up to two $C_{1-4}$alkyl groups; di($C_{1-4}$ alkyl) hydroxypyridinyl; di($C_{1-4}$alkyl)-$C_{1-4}$alkyloxypyridinyl; pyridazinyl optionally substituted with $C_{1-4}$alkyloxy; pyrimidinyl optionally substituted with hydroxy or $C_{1-4}$alkyloxy; thiazolyl optionally substituted with $C_{1-4}$alkyl; thiadiazolyl optionally substituted with $C_{1-4}$alkyl; benzoxazolyl or benzothiazolyl; or $R^6$ is pyrazinyl or pyridazinyl substituted with $C_{1-4}$alkyl;

Z is C=O or CHOH; and

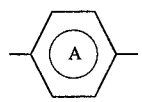

is a radical of formula

 (a-1)

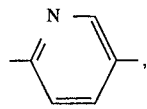 (a-2)

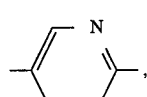 (a-3)

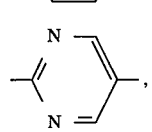 (a-4)

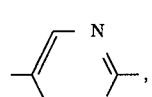 (a-5)

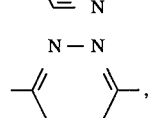 (a-6)

or

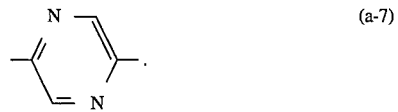 (a-7)

2. A compound according to claim 1, wherein $R^6$ is pyridinyl optionally substituted with up to two $C_{1-1}$alkyl groups; di($C_{1-4}$alkyl) hydroxypyridinyl; di($C_{1-4}$alkyl)-$C_{1-4}$alkyloxypyridinyl; pyridazinyl optionally substituted with $C_{1-4}$alkyloxy; pyrimidinyl optionally substituted with hydroxy or $C_{1-4}$alkyloxy; thiazolyl optionally substituted with $C_{1-4}$alkyl; thiadiazolyl optionally substituted with $C_{1-4}$alkyl; benzoxazolyl or benzothiazolyl.

3. A compound according to claim 2 wherein
$R^1$, $R^3$ and $R^5$ are hydrogen;
$R^2$ is $C_{1-4}$alkyl;
$R^4$ is halo; and
Y is N.

4. A compound according to claim 3 wherein
$R^2$ is ethyl;
$R^6$ is pyridinyl, thiazolyl or pyrimidinyl; and

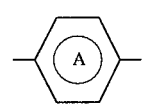

is a radical of formula (a-1) or (a-2).

5. A compound according to claim 1 wherein said compound is

2-[1-(4-chlorobenzoyl)propyl]-2,4-dihydro-4-[6-[4-(2-pyrimidinyl)-1-piperazinyl]-3-pyridinyl]-3-pyridinyl]-3H-1,2,4-triazol-3-one;

2-[1-(4-chlorobenzoyl)propyl]-2,4-dihydro-4-[6-[4-(2-pyridinyl)-1-piperazinyl]-3H-1,2,4-triazol-3-one;

2-[1-[(4-chlorophenyl)hydroxymethyl]propyl]-2,4-dihydro-4-[6-[4-(2-pyridinyl)-1-piperazinyl]-3-pyridinyl]-3H-1,2,4-triazol-3-one; and 2-[1-[(4-chlorophenyl)hydroxymethyl]propyl]-2,4-dihydro-4-[6-[4-(2-thiazolyl) -1-piperazinyl]-3-pyridinyl]-3H-1,2,4-triazol-3-one;

a pharmaceutically acceptable addition salt or a stereochemically isomeric form thereof.

6. A pharmaceutical composition comprising a therapeutically effective amount of a compound as claimed in any one of claims 1 to 5 and a pharmaceutically acceptable carrier.

7. A method for treating infection with *Helicobacter pylori* and related species in patients in need of such treatment which requires administering to such patients a therapeutically effective amount of a compound as defined in claim 3.

8. A method for treating infection with *Helicobacter pylori* and related species in patients in need of such treatment which requires administering to such patients a therapeutically effective amount of a compound as defined in claim 4.

9. A therapeutic composition comprising a compound as claimed in any one of claims 1 to 5, a pharmaceutically acceptable bismuth compound and/or a proton pump inhibitor.

10. A method for treating infection with *Helicobacter pylori* and related species in patients in need of such treatment which requires administering to such patients a therapeutically effective amount of a compound as defined in claim 5.

11. A method for treating infection with *Helicobacter pylori* and related species in patients in need of such treatment which requires administering to such patients a therapeutically effective amount of a compound as defined in claim 1.

12. A method for treating infection with *Helicobacter pylori* and related species in patients in need of such treatment which requires administering to such patients a therapeutically effective amount of a compound as defined in claim 2.

* * * * *